US00PP31820P2

(12) United States Plant Patent
Knott

(10) Patent No.: US PP31,820 P2
(45) Date of Patent: May 26, 2020

(54) ***SALVIA* PLANT NAMED 'KISSES AND WISHES'**

(50) Latin Name: *Salvia hybrida*
Varietal Denomination: Kisses and Wishes

(71) Applicant: Sarah Jane Knott, Horsham (GB)

(72) Inventor: Sarah Jane Knott, Horsham (GB)

( * ) Notice: Subject to any disclaimer, the term of this patent is extended or adjusted under 35 U.S.C. 154(b) by 0 days.

(21) Appl. No.: 16/501,653

(22) Filed: May 16, 2019

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 6/508; A01H 5/02
See application file for complete search history.

*Primary Examiner* — Keith O. Robinson
(74) *Attorney, Agent, or Firm* — Cassandra Bright

(57) ABSTRACT

A new and distinct *Salvia* cultivar named 'Kisses and Wishes' is disclosed, characterized by bright medium pink flowers and coral-pink calyces. Plants are bushy and branch prolifically, especially when pinched as a young plant. The flowering period begins in May and continues until first frost. The new variety is a *Salvia hybrida*, normally produced as an outdoor garden or container plant.

3 Drawing Sheets

Latin name of the genus and species: *Salvia hybrida.*
Variety denomination: 'Kisses and Wishes'.

BACKGROUND OF THE INVENTION

The new *Salvia* cultivar is a product of chance discovery. The inventors discovered the new variety as a naturally-occurring whole plant mutation among a population of the parent variety, growing at the home in Horsham, United Kingdom.

The parent variety is *Salvia* 'Wendy's Wish', U.S. Plant Pat. No. 21,889. The new variety was identified as a potentially interesting selection during June of 2015 in Horsham, United Kingdom. First public exposure was May 21, 2018, in the United Kingdom. This was a publication by The Royal Horticultural Society. Information and access to the new variety was initiated directly by the inventors or one who obtained the claimed invention directly or indirectly from the inventors. All public disclosures made between May 21, 2018 and the filing of this application fall within the exception allowed under 102(b)(1).

Asexual reproduction of the new cultivar *Salvia* 'Kisses and Wishes' was first performed during September 2015, in Horsham, United Kingdom, using terminal vegetative cuttings. Subsequent propagation has shown that the unique features of this cultivar are stable and reproduced true to type on successive generations.

SUMMARY OF THE INVENTION

The cultivar *Salvia* 'Kisses and Wishes' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Kisses and Wishes'. These characteristics in combination distinguish 'Kisses and Wishes' as a new and distinct *Salvia* cultivar:

1. Flower color is bright medium pink.
2. Calyx is coral pink, particularly at tips.
3. Long season of flowering, from May until first frost.
4. Bushy plant habit with prolific branching, particularly if pinched as a young plant.

PARENT COMPARISON

Plants of the new cultivar 'Kisses and Wishes' are similar to plants of the parent in most horticultural characteristics, however, plants of the new cultivar 'Kisses and Wishes' differ in the following:

1. Flower color of new variety is bright medium pink, while the parent variety is darker pink.
2. The new variety's calyx is coral pink, while the parent variety has red-bronze calyces.
3. Flower stems of the new variety are paler in color, while the parent variety has darker stems.

COMMERCIAL COMPARISON

Plants of the new cultivar 'Kisses and Wishes' can be compared to the commercial variety *Salvia* 'SAL010-0', U.S. Plant Pat. No. 25,183. These varieties are similar in most horticultural characteristics; however 'Kisses and Wishes' differs in the following:

1. Flowers of the new variety are bright medium pink, while this comparator's flowers are bright to deep red.
2. The new variety has a coral-pink calyx, while this comparator has a salmon/bronze calyx.

Plants of the new cultivar 'Kisses and Wishes' can also be compared to the commercial variety *Salvia* 'SER-WISH', U.S. Plant Pat. No. 27,057. These varieties are similar in most horticultural characteristics; however 'Kisses and Wishes' differs in the following:

1. The new variety has bright medium pink flowers, while this comparator has bright red-purple to purple flowers.
2. The new variety has a coral-pink calyx, while this comparator has a dark purple calyx.
3. The new variety has an upright, bushy habit, while this comparator is more compact and produces more branches.

BRIEF DESCRIPTION OF THE PHOTOGRAPHS

The accompanying photograph in FIG. 1 illustrates in full color typical plants of 'Kisses and Wishes' grown outdoors in Horsham, United Kingdom. Age of the plants photographed are approximately 26 weeks from unrooted cuttings.

Figure 1:
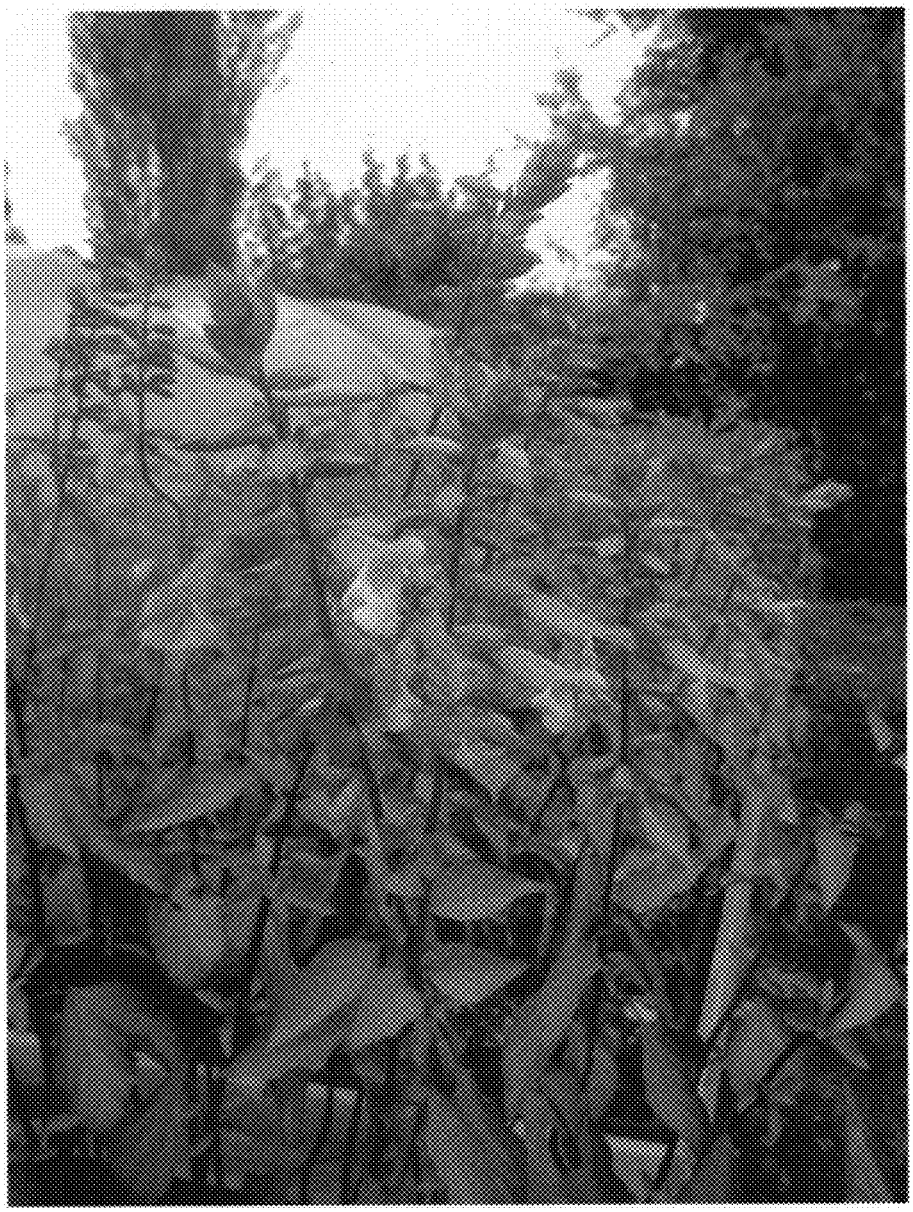
Figure 2:
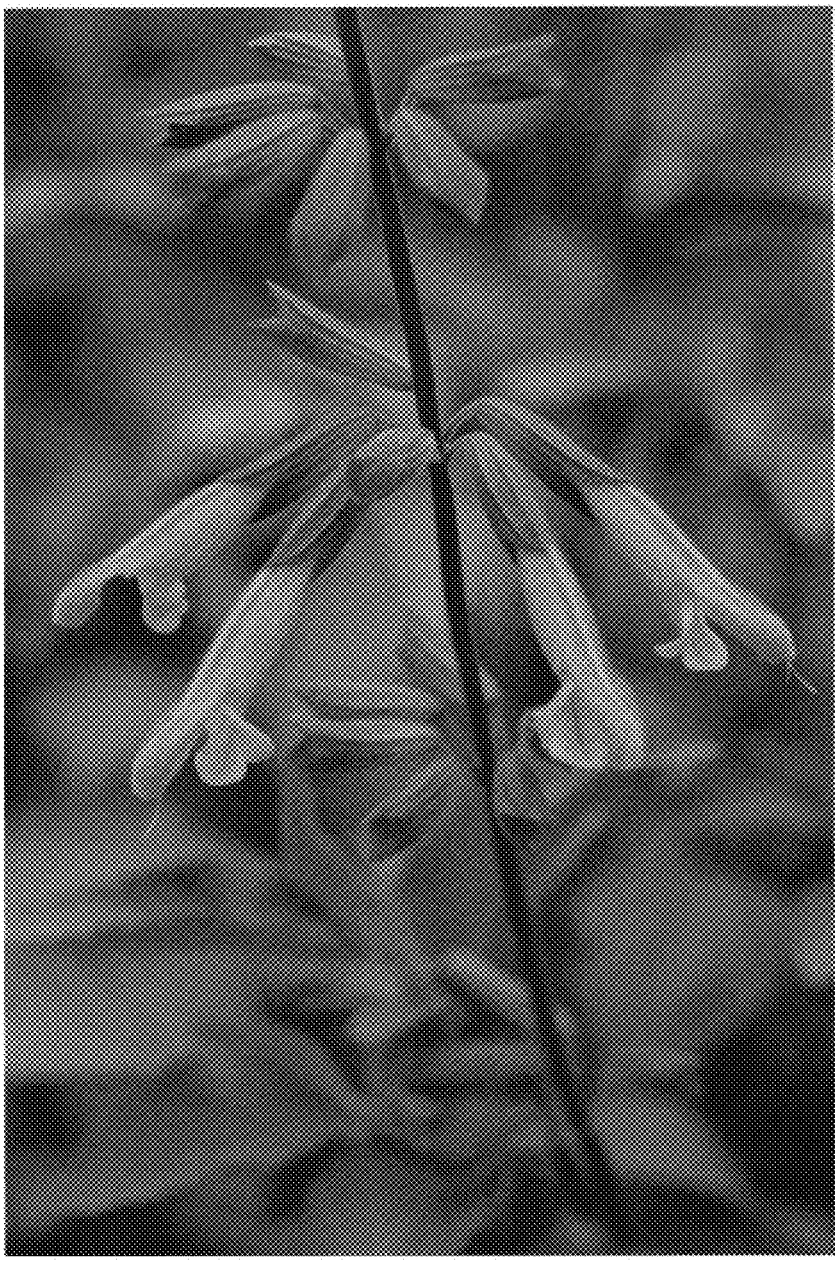
FIG. 2 illustrates in full color typical flowers of 'Kisses and Wishes'.
Figure 3:
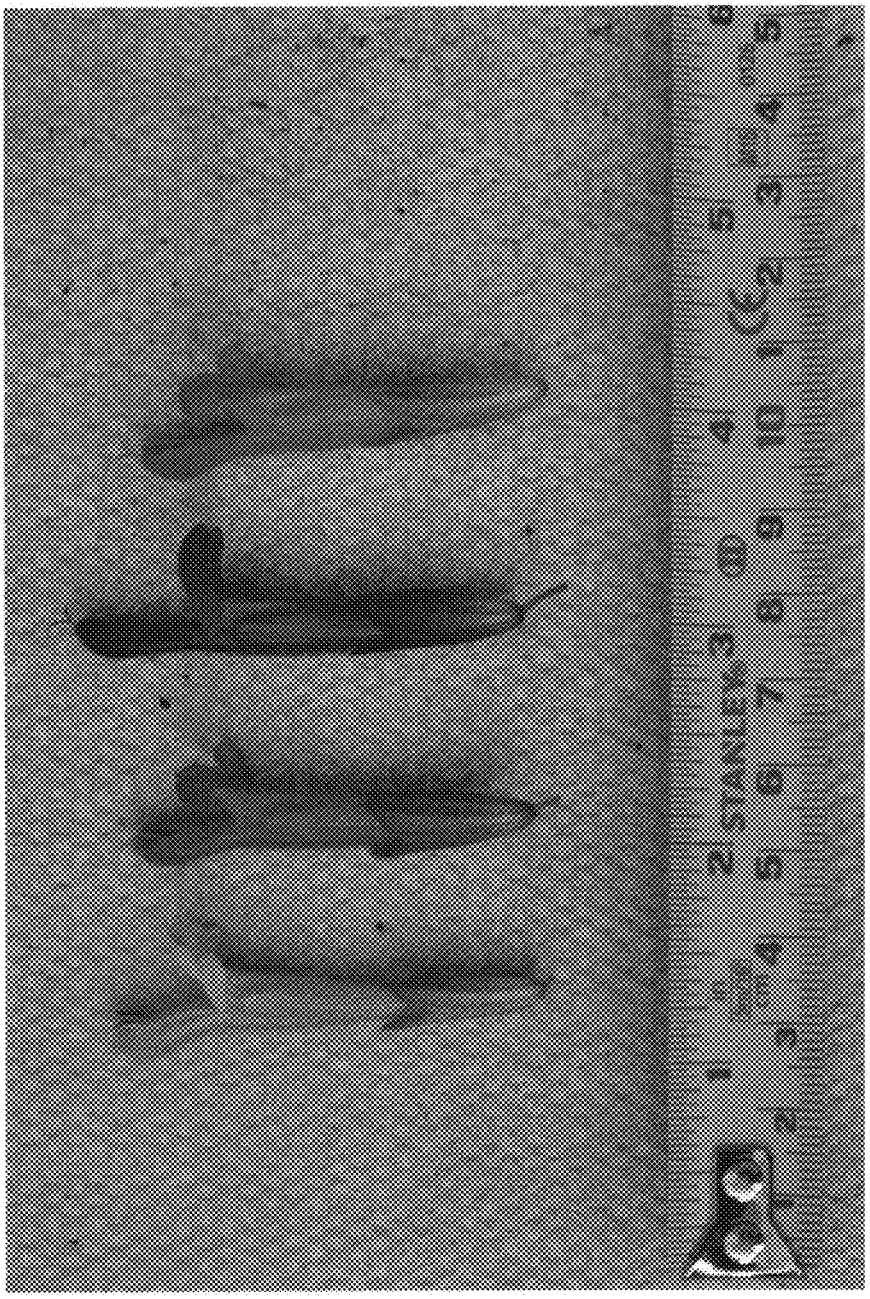
FIG. 3 shows a comparison of flower colors of 4 different *Salvia* varieties. From left to right is 'Kisses and Wishes', 'Wendy's Wish', 'SER-WISH', with 'SAL010-0' on the far right.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'Kisses and Wishes' plants grown in Horsham, United Kingdom. The growing temperature ranged from approximately 20° C. to 21° C. Measurements and numerical values represent averages of typical plant types.

Botanical classification: *Salvia hybrida* 'Kisses and Wishes'.

ROOTS

Root description: Fine and fibrous. Colors include Green-White 157D on new growth and Orange-White 159C, Grey-Brown 199B and 199C for older roots.

Time to rooted cutting: 2 to 4 weeks.

PLANT

Growth habit: Evergreen perennial. Upright, compact, slightly outwardly spreading.

Pot size of plant described: 1 liter container.

Height: 90 cm.

Plant spread: 75 cm.

Vigor: Moderate.

Branching characteristics:

*Shape*.—Quadrangular.
*Surface*.—Fluted and glabrous.
*Color*.—RHS Green NN137C.
*Strength*.—Strong and rigid.
*Length* (*average*).—45 cm.
*Width* (*average*).—0.4 cm.
*Internodes*.—3.5 cm to 12 cm.

Age of plant described: Approximately 6 months.

FOLIAGE

Leaf:

*Type*.—Simple.
*Arrangement*.—Opposite.
*Margin*.—Dentate to crenate.
*Surface* (*abaxial and adaxial*).—Glabrous.
*Shape*.—Ovate.
*Length* (*range*).—2 cm to 10 cm.
*Width* (*range*).—1 cm to 6 cm.
*Abaxial surface color*.—RHS Yellow-Green 148B.
*Adaxial surface color*.—RHS Yellow-Green 147A.
*Apex*.—Subacute.
*Base* (*range*).—Attenuate to aequilateral.
*Venation pattern*.—Pinnate.
*Vein color* (*abaxial surface*).—RHS Yellow-Green 147D.
*Vein color* (*adaxial surface*).—RHS Green NN137A but Greyed-Purple 187B at base of midrib.
*Attachment*.—Petiolate.
*Petiole shape*.—Sulcate.
*Petiole surface*.—Very finely pubescent.
*Petiole color*.—RHS Yellow-Green 146B; adaxial surface tinted Greyed-Purple 187B.
*Petiole dimensions*.—3.50 cm in length and 2.5 mm in width.
*Fragrance*.—None observed.

FLOWER

Natural flowering season: Flowering from Late Spring to late Summer.

Inflorescence type and habit: Raceme.

Flower longevity on plant: Individual flowers last approximately 3 to 5 days on the plant. Corolla self-cleaning, calyx persistent.

Quantity of flowers: About 40 to 80 buds through fully opened flowers per inflorescence.

Inflorescence size:

*Diameter*.—Approximately 6.0 cm.
*Height*.—Average 30 cm.

Individual flowers:

Corolla size:

*Diameter*.—Average 4.0 cm.
*Length*.—Average 0.9 cm.
*Fragrance*.—Moderately strong musty aromatic scent.

Corolla:

*Petal arrangement*.—The corolla is sympetalous and typically bilabiate with 2 small, fully fused lobes forming a single upper lip and 3 larger fused lobes forming a lower lip.
*Margin*.—Entire.
*Tip shape*.—Upper lip tip emarginate, lower lip tip broadly obtuse.
*Length*.—Upper lip Approximately 1.1 cm. Lower lip Approximately 0.9 cm. Tube length Approximately 1.8 cm.
*Width*.—Upper lip: Approximately 0.4 cm, lower lip Approximately 0.9 cm. Tube width: Approximately 0.6 cm.
*Texture*.—Upper lip: Abaxial: Glabrous. Adaxial: Velutinous. Lower lip: Abaxial: Glabrous. Adaxial: Velutinous.

Color:

*Upper lip*.—Inner surface: Near RHS Red-Purple 67C at sides, fading to 67D in older flowers; 68A in the center, fading to 73A in older flowers. Outer surface: Near RHS Red-Purple 68A.

Color:

*Lower lip*.—Inner surface: Near RHS Red-Purple 73A. Outer surface: Near RHS Red-Purple 73A.

Color:

*Tube*.—Inner surface: Near RHS Red-Purple 73C. Outer surface: Near RHS 68A fading to 73A in older flowers.

Bud: Flower bud includes immature calyx which completely surrounds immature corolla.

*Shape*.—Ovoid.
*Length*.—Approximately 2 cm.
*Diameter*.—Approximately 0.5 cm.
*Color*.—Near RHS 64A at sides close to the apex darkening to 64B at the base; bottom 64C; top marked with a line of N66C.

Calyx:

*Length*.—Approximately 1.8 cm.
*Diameter*.—Approximately 0.6 cm.
*Shape*.—Tubular, flaring bell-shape.
*Color*.—In new flowers, upper surface Greyed-Purple 186B, lower surface 186C, veins 184C; in older flowers, upper and lower surfaces 186D, veins 184A.

Sepals:

*Shape*.—Quantity per flower: 3, fused to form a tube. Unfused apex.
*Margin*.—Entire.
*Apex*.—Acute.
*Texture*.—Softly pubescent and ridged.

Peduncle:

*Length*.—Average 26 cm.
*Diameter*.—0.2 cm.
*Color*.—Near RHS Green NN137C at base, turning 187B near attachment.
*Shape*.—Quadrangular and fluted.
*Orientation*.—Straight. Occurring at approximately 15 degree angle from center of plant.
*Strength*.—Moderately strong.
*Texture*.—Sparsely pubescent.

Pedicels:

*Length*.—Average 0.5 cm.
*Diameter*.—0.1 cm.
*Color*.—Near RHS Greyed-Purple 187B.
*Orientation*.—Straight, approximately 25 degree angle from attachment.
*Strength*.—Strong.
*Texture*.—Pubescent.

REPRODUCTIVE ORGANS

Stamens:

*Number*.—2.
*Length*.—16 mm.
*Color*.—RHS White N155A, fading to Red-Purple 70C at base.
*Staminode color*.—RHS Greyed-Purple 183A.
*Staminode length*.—3 mm.
*Pollen*.—Absent.

Pistil:

*Number*.—1.
*Length*.—4.4 cm.
*Style*.—Length: 2 mm. Width: 4 mm. Color: RHS Red-Purple 71D.

Ovary:

*Position*.—Superior.
*Shape*.—Broadly globose.
*Height*.—2.5 mm.
*Diameter*.—3 mm.
*Color*.—RHS Yellow-Green 150B.
*Surface*.—Glabrous.
*Appearance*.—Semi-glossy.

OTHER CHARACTERISTICS

Seeds and fruits: Not observed.

Disease/pest resistance: Neither resistance nor susceptibility to pathogens and pests common to *Salvia* have been observed.

Temperature tolerance: Hardy to USDA Zone 9.

What is claimed is:

1. A new and distinct cultivar of *Salvia* plant named 'KISSES AND WISHES' as herein illustrated and described.

* * * * *